United States Patent [19]

Meriläinen

[11] Patent Number: 4,856,531
[45] Date of Patent: Aug. 15, 1989

[54] MEASURING DEVICE FOR METABOLIC QUANTITIES CONNECTABLE TO A RESPIRATOR

[75] Inventor: Pekka Meriläinen, Helsinki, Finland
[73] Assignee: Instrumentarium Corp., Finland
[21] Appl. No.: 87,984
[22] Filed: Aug. 17, 1987

Related U.S. Application Data

[63] Continuation of Ser. No. 794,486, Nov. 4, 1985, abandoned.

[51] Int. Cl.⁴ ............................................. A61B 5/08
[52] U.S. Cl. .................................... 128/719; 128/730
[58] Field of Search ................... 128/719, 730, 204.22

[56] References Cited

U.S. PATENT DOCUMENTS 4,233,842 11/1980 Raemer et al. ...................... 128/719
4,572,208 2/1986 Cutler et al. .......................... 128/719

Primary Examiner—Edward M. Coven
Assistant Examiner—Randy Citrin
Attorney, Agent, or Firm—Andrus, Sceales, Starke & Sawall

[57] ABSTRACT

The invention relates to a device intended for monitoring the carbon dioxide output, oxygen consumption and respiration quotient of a patient connected to a respirator. The device comprises $O_2$ (15) and $CO_2$ (14) analyzers, a mixing chamber (6), a constant flow fan (8), a gas collector hose (2) and magnetic valves (10-13). The carbon dioxide output and oxygen consumption are directly calculated from the carbon dioxide content of gas mixed with constant air flow from said mixing chamber, from the carbon dioxide and oxygen contents of the gas in said mixing chamber, and from the oxygen content of the gas delivered into a patient by said respirator.

5 Claims, 1 Drawing Sheet

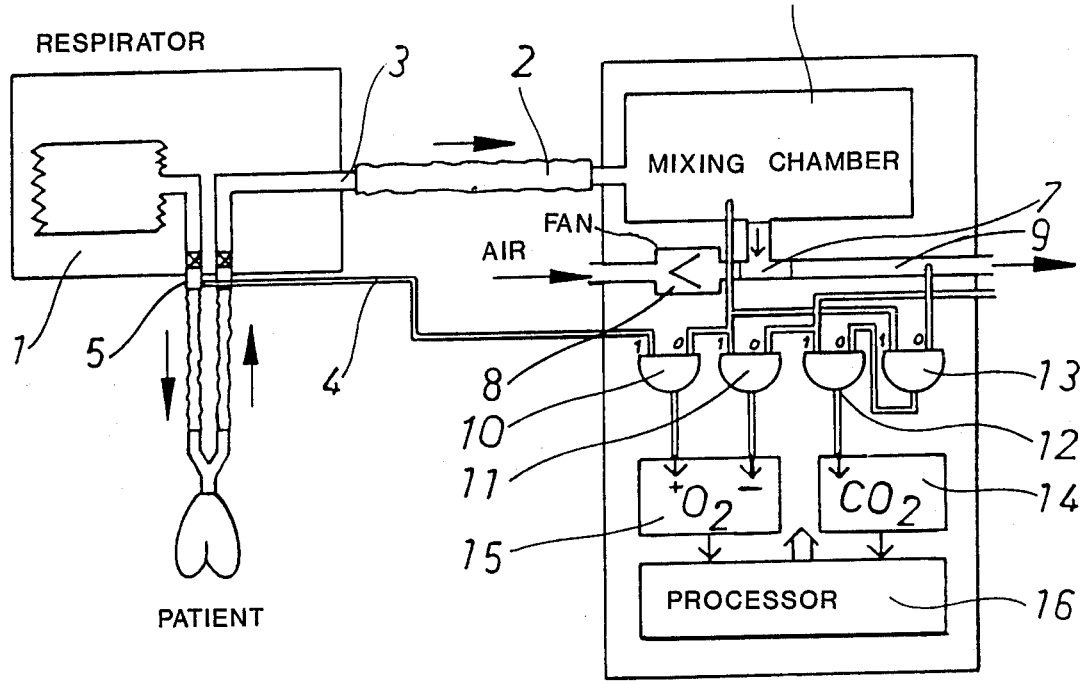
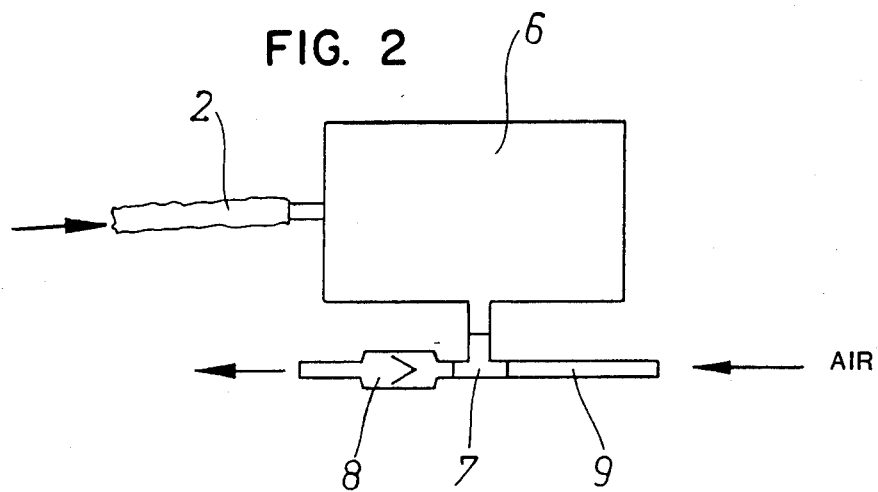

4,856,531

MEASURING DEVICE FOR METABOLIC QUANTITIES CONNECTABLE TO A RESPIRATOR

This application is a continuation application of application Ser. No. 06/794,486, filed Nov. 4, 1985 now abandoned.

BACKGROUND OF THE INVENTION

A critically ill patient treated in a hospital's intensive care ward usually receives nourishment parenterally or in liquid form directly in a vein. Since illness and injuries may change a patient's metabolism and energy consumption considerably from a standard consumption, dictated by the height, weight, age and sex, normally used as a basis of estimating the need of nourishment, a strong interest has arisen to employ measuring in order to find out the quantitative and qualitative need of nourishment of a critically ill patient. This is possible by means of so-called indirect calorimetry wherein, by measuring the exchange of respiratory gases, it is possible to calculate energy consumption on the basis of oxygen consumption in a certain state of equilibrium and to conclude the quality of a nourishment digested on the basis of a ratio of carbon dioxide output to oxygen consumption.

Most patients in an intensive care ward are connected to a respirator in order to maintain respiration and, thus, said gas exchange measuring should be effected by means of a device that can be connected to a respirator and is independent of the make and operating principle of a respirator.

As for the respirator manufacturers, at least Swedish companies Engström Medical Ab and Siemens-Elema have developed metabolism measuring instruments connectable to Engström Erica and Siemens Servo Ventilator 900 series, which instruments, however, partially use information obtained from the sensors of a respirator itself and, thus, such instruments can only be employed as an accessory to said equipment.

In terms of measuring technique, a particular problem has been flowmetry, which is needed, in addition to gas content measuring, in calculation of oxygen consumption and carbon dioxide output. The accuracy and reliability of flow sensors are put to a severe test in clinical conditions, particularly due to moisture and the polluting effect of secretions coming out of a patient.

SUMMARY OF THE INVENTION

In this invention, the carbon dioxide production and oxygen consumption are measured in a manner that does not at all require direct measuring of the flow of respiratory gas. In accordance with the invention, the exhalation gas discharged from a respirator connected to a patient is delivered to a mixing chamber, and the gas flowing out of the mixing chamber is mixed with a constant flow of air in a channel. The carbon dioxide content of the air-gas mixture in the channel is measured, and the carbon dioxide and oxygen contents of the gas in the mixing chamber are also measured, along with the oxygen content of the gas delivered by the respirator to the patient. Through these measurements, the carbon dioxide output and oxygen consumption can be determined.

DESCRIPTION OF THE DRAWINGS

In the drawings:

FIG. 1 is a schematic representation of the monitoring device of the invention; and FIG. 2 is a schematic representation of a modified form of the invention.

DESCRIPTION OF THE ILLUSTRATED EMBODIMENT

A diagrammatic view of the device is shown in FIG. 1. The device is connected to a respirator 1 by coupling a wide diameter gas hose 2 to the exhalation tube 3 and the sampling hose 4 of a gas sensor to the inhalation tube 5 of a respirator. The exhalation gas entering said device flows first into a mixing chamber 6, having typically a volume of 5 liters and, thus, a steady carbon dioxide and oxygen content corresponding in average to circa 10 respiration cycles. During each exhalation cycle, the amount of gas equal to a single respiration volume flows out of the mixing chamber, said gas having a carbon dioxide content of $\overline{F_{ECO2}}$ and oxygen content of $\overline{F_{EO2}}$. This gas mixes in a T-element 7 with a constant flow K generated by a fan unit 8, which typically can be 20 l/min. Thus, the instantaneous carbon dioxide content $F^*_{ECO2}(t)$ measured in a hose (9), as a result of dilution caused by air draft, will be $$F^*_{ECO2}(t) = \frac{\overline{F_{ECO2}} \times V_E(t)}{V_E(t) + K} \quad (1)$$

wherein $V_E(t)$ is the flow rate of a gas flowing out of the mixing chamber at a moment t. Thus, the output of carbon dioxide $\dot{V}_{CO2}$ in time interval $t_0 \rightarrow t_0 + T$ will be $$\dot{V}_{CO2} = \frac{1}{T} \int_{t_0}^{t_0 + T} \overline{F_{ECO2}} \times V_E(t) \, dt \quad (2)$$

wherein time T is assumed so short that the average carbon dioxide content $\overline{F_{ECO2}}$ in the mixing chamber does not change noticeably during that time.

Obtained from equation (1)

$$V_E(t) = \frac{K \times F^*_{ECO2}(t)}{\overline{F_{ECO2}} - F^*_{ECO2}(t)} \quad (3)$$

By including this in equation (2), the carbon dioxide output in time interval $t_0 \rightarrow t_0 + T$ will be obtained as follows $$\dot{V}_{CO2} = \frac{K}{T} \int_{t_0}^{t_0 + T} \frac{\overline{F_{ECO2}} \times F^*_{ECO2}(t)}{\overline{F_{ECO2}} - F^*_{ECO2}(t)} \, dt \quad (4)$$

The carbon dioxide output can thus be calculated without flowmetry by measuring the carbon dioxide content in mixing chamber 6 and outlet hose 9 alternately at a suitable rate or by simultaneous use of two carbon dioxide sensors, which is not, however, a practical solution.

On the other hand, the oxygen consumption $\dot{V}_{O2}$ can be determined by measuring also the oxygen content $F_{IO2}$ of inhalation gas and the oxygen content $\overline{F_{EO2}}$ of mixed exhalation gas. By utilizing a prior known presumption, according to which the nitrogen consumption is zero, the respiration quotient RQ will be a known result.

$$RQ = \frac{\dot{V}_{CO2}}{\dot{V}_{O2}} = \frac{\frac{\overline{F_{ECO2}}}{F_{IO2} - \overline{F_{EO2}}}}{1 + \left(\frac{1 - \frac{\overline{F_{ECO2}}}{F_{IO2} - \overline{F_{EO2}}}}{1 - F_{IO2}}\right) \times F_{IO2}} \quad (5)$$

After this, the oxygen consumption $\dot{V}_{O2}$ will be obtained simply:

$$\dot{V}_{O2} = \frac{\dot{V}_{CO2}}{RQ} \quad (6)$$

The measuring of gas contents at various measuring points is effected intermittently by means of magnetic valves 10–13 controlled by a microprocessor 16. A typical measuring sequence is illustrated in enclosure 1.

A carbon dioxide sensor (14) comprises an analyzer based on the infrared absorption of $CO_2$ and an oxygen sensor 15 comprises a high-speed differential paramagnetic oxygen sensor which, if necessary, allow the use of a measuring sequence considerably quicker than that illustrated. Sensor 14 is preferably a direct differential sensor such as the commercially available Model OM-101 from Datex Instrumentarium Corporation of Helsinski, Finland. Sensor 15 may also be an infrared sensor such as the commercially available Model CX-104 from Datex Instrumentarium Corporation of Helinski, Finland, and constructed in accordance with the teaching of U.S. Pat. No. 4,633,705. The constant flow generator comprises a centrifugal fan and a flow resistance constructed integrally therewith, said resistance being a lot higher than the flow resistance from the intersection of said T-element 7 to the outlet, whereby the rate of flow coming out of the mixing chambers does not have a substantial effect on flow K.

The mixing chamber and fan are designed in a manner that the water condensating from the moist exhalation gas trickles out of the mixing chamber and discharges through the outlet hose of the device.

FIG. 2 shows an alternative measuring configuration. In this design, a fan 8 maintains the mixed flow constant K but, in this case, flow K must be higher than the peak flow of exhalation, which may be up to 100 l/min., since otherwise the direction of flow may be reversed in tube 9 and some exhalation gas slips past a measuring point. Another drawback is the fact that the condensed moisture must discharge through the fan. It would be an advantage, however, that the carbon dioxide output could be obtained by a more simple calculation than in the first-described alternative. In this case, the carbon dioxide output in time interval $t_o \rightarrow t_o + T$ will be $$\dot{V}_{CO2} = \frac{K}{T} \int_{t_o}^{t_o + T} F^*_{ECO2}(t) \, dt \quad (7)$$

RQ and $\dot{V}_{O2}$ are obtained the same way as above. The device is also capable of measuring oxygen consumption and carbon dioxide output on a spontaneously breathing patient or on a stress-tested person provided that a patient is fitted with an air-tight mask provided with one-way valves.

Diluting principle can also be effected by measuring dilution of the oxygen coming out of the mixing chamber as it mixes with the constant air flow. Thus, the instantaneous oxygen content in hose 9 will be $$F^*_{EO2}(t) = \frac{\overline{F_{EO2}} \times V_E(t) + 0.21 \times K}{V_e(t) + K} \quad (8)$$

Dissolving an instantaneous flow $V_E(t)$ from the above will give $$V_E(t) = \frac{K \times (F^*_{EO2}(t) - 0.21)}{\overline{F_{EO2}} - F^*_{EO2}(t)} \quad (9)$$

The minute volume of respiration is obtained from this by integrating and, in a prior known manner, it is thus possible to further calculate the oxygen consumption and carbon dioxide output if we know, in addition to the above, the carbon dioxide content of gas in the mixing chamber and the difference between its oxygen content and that of the inhalation gas.

However, a measuring sequence based on the dilution of oxygen is in practice more difficult to perform, since oxygen must be measured at three points. In addition, in the case of an inhalation gas with only slightly elevated oxygen concentration, it is possible that the oxygen content of the mixing chamber exhalation gas is so close to that of room air that the result provided by equation 9 becomes highly inaccurate.

The measuring system can be calibrated e.g. by using a calibration syringe having a capacity of 1 liter to pump into said mixing chamber 6 a gas, whose oxygen or carbon dioxide content differs clearly from room air. A gas readily available in hospital conditions is pure oxygen which can be withdrawn by means of a system comprising said T-element and one-way valves into the syringe and pumped into the mixing chamber typically at a frequency of 10 times a minute. Thus, the program of the device can calibrate a constant flow factor K on the basis of formula (9), presuming that the gas sensors have been separately calibrated with a precision gas.

I claim:

1. An apparatus for monitoring the carbon dioxide output, oxygen consumption and respiration quotient of a patient, comprising a respirator having an inlet conduit for supplying gas to a patient and having an outlet conduit for discharging exhalation gas from said patient, a mixing chamber connected to said outlet conduit and having an outlet means to discharge said gas from said chamber, air supply means connected to said outlet means for mixing air at a constant flow rate with said gas to provide a diluted gas, means for measuring the carbon dioxide content of said diluted gas, means for measuring the carbon dioxide content of said exhalation gas in said mixing chamber, means for measuring the oxygen content of said exhalation gas in said mixing chamber, means for measuring the oxygen content of the gas delivered through said inlet conduit to the patient, and means for determining the carbon dioxide output and oxygen consumption by direct calculation from said measured contents.

2. The apparatus of claim 1, wherein said air supply means comprises a blower and said outlet means comprises a channel disposed downstream of said blower.

3. The apparatus of claim 2, wherein said mixing chamber includes a bottom portion, said outlet means is located at the bottom portion of the mixing chamber and said outlet means includes a T-fitting having a stem communicating with said mixing chamber and having a pair of aligned arms, one of said arms communicating with said blower and the other of said arms communicating with the atmosphere, said T-fitting being disposed below said mixing chamber whereby water condensing in said mixing chamber automatically drains by gravity through said fitting and said second arm.

4. A method of monitoring the carbon dioxide output, oxygen consumption and respiration quotient of a patient connected to a respirator, comprising the steps of delivering exhalation gas discharged from a respirator to a mixing chamber, flowing said exhalation gas out of said chamber and mixing said gas with air having a constant rate of flow to dilute said gas, measuring the carbon dioxide content of said diluted gas, measuring the carbon dioxide content of the exhalation gas in said chamber, measuring the oxygen content of said exhalation gas in said chamber, measuring the oxygen content of gas delivered by said respirator to said patient, and determining the carbon dioxide output and oxygen consumption by direct calculation from said measured contents.

5. The method of claim 4, wherein an air supply means is operated by supply said air, said air supply means being operated in a manner to draw gas from said mixing chamber and mix said gas with said air to provide a constant flow of said mixture.

* * * * *